United States Patent
Alamin et al.

(10) Patent No.: US 8,187,307 B2
(45) Date of Patent: May 29, 2012

(54) STRUCTURES AND METHODS FOR CONSTRAINING SPINAL PROCESSES WITH SINGLE CONNECTOR

(75) Inventors: Todd Alamin, Woodside, CA (US); Ian Bennett, San Francisco, CA (US); Louis Fielding, San Carlos, CA (US); Colin Cahill, San Francisco, CA (US); Manish Kothari, San Rafael, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 309 days.

(21) Appl. No.: 12/426,167

(22) Filed: Apr. 17, 2009

(65) Prior Publication Data

US 2009/0264929 A1    Oct. 22, 2009

Related U.S. Application Data

(63) Continuation-in-part of application No. PCT/US2007/081815, filed on Oct. 18, 2007.

(60) Provisional application No. 60/862,085, filed on Oct. 19, 2006.

(51) Int. Cl.
*A61B 17/88* (2006.01)
*A61B 17/70* (2006.01)
(52) U.S. Cl. .................. 606/279; 606/246; 606/248
(58) Field of Classification Search .......... 606/246–261, 606/263–266, 276–279, 330, 74–75, 103; 623/13.13–13.14
See application file for complete search history.

(56) References Cited

U.S. PATENT DOCUMENTS

| | | | |
|---|---|---|---|
| 3,648,691 A | 3/1972 | Lumb et al. | |
| 4,246,660 A | 1/1981 | Wevers | |
| 4,643,178 A | 2/1987 | Nastari et al. | |
| 4,708,132 A | 11/1987 | Silvestrini | |
| 4,743,260 A | 5/1988 | Burton | |
| 4,772,286 A | 9/1988 | Goble et al. | |
| 4,776,851 A | 10/1988 | Bruchman et al. | |
| 4,794,916 A | 1/1989 | Porterfield et al. | |
| 4,870,957 A | 10/1989 | Goble et al. | |
| 4,955,910 A | 9/1990 | Bolesky | |
| 4,966,600 A | 10/1990 | Songer et al. | |
| 5,002,574 A | 3/1991 | May et al. | |
| 5,011,484 A | 4/1991 | Breard | |

(Continued)

FOREIGN PATENT DOCUMENTS

EP    0 322 334 A1    6/1989

(Continued)

OTHER PUBLICATIONS

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

(Continued)

*Primary Examiner* — Eduardo C Robert
*Assistant Examiner* — Jacqueline Johanas
(74) *Attorney, Agent, or Firm* — Wilson Sonsini Goodrich & Rosati (57) ABSTRACT

Spinous process constraint structures include a first attachment element for placement over a first spinous process and a second attachment element for placement over a second spinous process. The attachment elements are joined by a single connector which may optionally include a compliance member for providing controlled elasticity between the spinous processes.

61 Claims, 10 Drawing Sheets

U.S. PATENT DOCUMENTS

| | | |
|---|---|---|
| 5,011,494 A | 4/1991 | von Recum et al. |
| 5,030,220 A | 7/1991 | Howland |
| 5,092,866 A | 3/1992 | Breard et al. |
| 5,108,433 A | 4/1992 | May et al. |
| 5,116,340 A | 5/1992 | Songer et al. |
| 5,171,280 A | 12/1992 | Baumgartner |
| 5,180,393 A | 1/1993 | Commarmond |
| 5,282,863 A | 2/1994 | Burton |
| 5,354,917 A | 10/1994 | Sanderson et al. |
| 5,366,455 A | 11/1994 | Dove et al. |
| 5,395,374 A | 3/1995 | Miller et al. |
| 5,415,658 A | 5/1995 | Killpela et al. |
| 5,415,661 A | 5/1995 | Holmes |
| 5,449,361 A | 9/1995 | Preissman |
| 5,456,722 A | 10/1995 | McLeod et al. |
| 5,458,601 A | 10/1995 | Young, Jr. et al. |
| 5,462,542 A | 10/1995 | Alesi, Jr. |
| 5,496,318 A | 3/1996 | Howland et al. |
| 5,540,698 A | 7/1996 | Preissman |
| 5,562,737 A | 10/1996 | Graf |
| 5,593,407 A | 1/1997 | Reis |
| 5,609,634 A | 3/1997 | Voydeville |
| 5,628,756 A | 5/1997 | Barker, Jr. et al. |
| 5,645,084 A | 7/1997 | McKay |
| 5,645,599 A | 7/1997 | Samani |
| 5,669,917 A | 9/1997 | Sauer et al. |
| 5,672,175 A | 9/1997 | Martin |
| 5,707,379 A | 1/1998 | Fleenor et al. |
| 5,725,582 A * | 3/1998 | Bevan et al. .............. 606/263 |
| 5,810,815 A | 9/1998 | Morales |
| 5,836,948 A | 11/1998 | Zucherman et al. |
| 5,902,305 A | 5/1999 | Beger et al. |
| RE36,221 E | 6/1999 | Breard et al. |
| 5,928,232 A | 7/1999 | Howland et al. |
| 5,933,452 A | 8/1999 | Eun |
| 5,935,133 A | 8/1999 | Wagner et al. |
| 5,964,769 A | 10/1999 | Wagner et al. |
| 5,989,256 A | 11/1999 | Kuslich et al. |
| 6,053,921 A | 4/2000 | Wagner et al. |
| 6,193,721 B1 | 2/2001 | Michelson |
| 6,224,630 B1 | 5/2001 | Bao et al. |
| 6,248,106 B1 | 6/2001 | Ferree |
| 6,283,996 B1 | 9/2001 | Chervitz et al. |
| 6,296,643 B1 | 10/2001 | Hopf et al. |
| 6,312,431 B1 | 11/2001 | Asfora |
| 6,322,279 B1 | 11/2001 | Yamamoto et al. |
| 6,364,883 B1 | 4/2002 | Santilli |
| 6,378,289 B1 | 4/2002 | Trudeau et al. |
| 6,391,030 B1 | 5/2002 | Wagner et al. |
| 6,395,018 B1 | 5/2002 | Castaneda |
| 6,427,080 B1 | 7/2002 | Radak |
| 6,436,099 B1 | 8/2002 | Drewry et al. |
| 6,451,019 B1 | 9/2002 | Zucherman et al. |
| 6,468,309 B1 | 10/2002 | Lieberman |
| 6,517,578 B2 | 2/2003 | Hein |
| 6,558,389 B2 | 5/2003 | Clark et al. |
| 6,582,433 B2 | 6/2003 | Yun |
| 6,589,246 B1 * | 7/2003 | Hack et al. ................ 606/74 |
| 6,605,091 B1 | 8/2003 | Iwanski |
| 6,616,669 B2 | 9/2003 | Ogilvie et al. |
| 6,626,944 B1 | 9/2003 | Taylor |
| 6,629,975 B1 | 10/2003 | Kilpela et al. |
| 6,652,527 B2 | 11/2003 | Zucherman et al. |
| 6,652,585 B2 | 11/2003 | Lange |
| 6,656,185 B2 | 12/2003 | Gleason et al. |
| 6,669,729 B2 | 12/2003 | Chin |
| 6,682,533 B1 | 1/2004 | Dinsdale et al. |
| 6,689,140 B2 | 2/2004 | Cohen |
| 6,689,168 B2 | 2/2004 | Lieberman |
| 6,695,852 B2 | 2/2004 | Gleason |
| 6,712,819 B2 | 3/2004 | Zucherman et al. |
| 6,716,245 B2 | 4/2004 | Pasquet et al. |
| 6,761,720 B1 | 7/2004 | Senegas |
| 6,828,357 B1 | 12/2004 | Martin et al. |
| 6,835,205 B2 | 12/2004 | Atkinson et al. |
| 6,899,716 B2 | 5/2005 | Cragg et al. |
| 6,989,011 B2 | 1/2006 | Paul et al. |
| 7,029,475 B2 | 4/2006 | Panjabi |
| 7,163,558 B2 | 1/2007 | Senegas et al. |
| 7,201,751 B2 | 4/2007 | Zucherman et al. |
| 7,335,203 B2 | 2/2008 | Winslow et al. |
| 7,413,576 B2 | 8/2008 | Sybert et al. |
| 7,452,351 B2 | 11/2008 | Miller et al. |
| 7,458,981 B2 | 12/2008 | Fielding et al. |
| 7,520,887 B2 | 4/2009 | Maxy et al. |
| 7,524,324 B2 | 4/2009 | Winslow |
| 7,553,320 B2 | 6/2009 | Molz, IV et al. |
| 7,591,837 B2 | 9/2009 | Goldsmith |
| 8,029,549 B2 * | 10/2011 | Malandain et al. ........... 606/279 |
| 2001/0007073 A1 | 7/2001 | Zucherman et al. |
| 2002/0095154 A1 | 7/2002 | Atkinson et al. |
| 2002/0147449 A1 | 10/2002 | Yun |
| 2002/0151978 A1 | 10/2002 | Zacouto et al. |
| 2003/0050700 A1 | 3/2003 | Kihara |
| 2003/0088251 A1 | 5/2003 | Braun et al. |
| 2004/0024458 A1 | 2/2004 | Senegas et al. |
| 2004/0034351 A1 | 2/2004 | Sherman et al. |
| 2004/0082954 A1 | 4/2004 | Teitelbaum et al. |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143268 A1 | 7/2004 | Falahee |
| 2004/0167520 A1 | 8/2004 | Zucherman et al. |
| 2004/0172132 A1 | 9/2004 | Ginn |
| 2004/0215341 A1 | 10/2004 | Sybert et al. |
| 2004/0243239 A1 | 12/2004 | Taylor |
| 2005/0033435 A1 | 2/2005 | Belliard et al. |
| 2005/0049708 A1 | 3/2005 | Atkinson et al. |
| 2005/0123581 A1 | 6/2005 | Ringeisen et al. |
| 2005/0131405 A1 | 6/2005 | Molz, IV et al. |
| 2005/0154390 A1 | 7/2005 | Biedermann et al. |
| 2005/0192581 A1 | 9/2005 | Molz et al. |
| 2005/0203624 A1 | 9/2005 | Serhan et al. |
| 2005/0216017 A1 | 9/2005 | Fielding et al. |
| 2005/0228383 A1 * | 10/2005 | Zucherman et al. ............ 606/61 |
| 2005/0267470 A1 | 12/2005 | McBride |
| 2005/0267518 A1 | 12/2005 | Wright et al. |
| 2006/0036324 A1 | 2/2006 | Sachs et al. |
| 2006/0041259 A1 | 2/2006 | Paul et al. |
| 2006/0064166 A1 | 3/2006 | Zucherman et al. |
| 2006/0069447 A1 | 3/2006 | Disilvestro et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell |
| 2006/0149230 A1 | 7/2006 | Kwak et al. |
| 2006/0195102 A1 | 8/2006 | Malandain |
| 2006/0217726 A1 | 9/2006 | Maxy et al. |
| 2006/0240533 A1 | 10/2006 | Sengupta et al. |
| 2006/0241610 A1 | 10/2006 | Lim et al. |
| 2006/0271055 A1 | 11/2006 | Thramann |
| 2007/0010822 A1 | 1/2007 | Zalenski et al. |
| 2007/0073293 A1 | 3/2007 | Martz et al. |
| 2007/0083200 A1 | 4/2007 | Gittings et al. |
| 2007/0173818 A1 | 7/2007 | Hestad et al. |
| 2007/0213829 A1 | 9/2007 | Le Couedic et al. |
| 2007/0233096 A1 | 10/2007 | Garcia-Bengochea |
| 2007/0270828 A1 | 11/2007 | Bruneau et al. |
| 2007/0299445 A1 | 12/2007 | Shadduck et al. |
| 2008/0009866 A1 | 1/2008 | Alamin et al. |
| 2008/0021466 A1 | 1/2008 | Shadduck et al. |
| 2008/0027435 A1 | 1/2008 | Zucherman et al. |
| 2008/0033552 A1 | 2/2008 | Lee et al. |
| 2008/0045949 A1 | 2/2008 | Hunt et al. |
| 2008/0051784 A1 | 2/2008 | Gollogly |
| 2008/0097431 A1 | 4/2008 | Vessa |
| 2008/0108993 A1 | 5/2008 | Bennett et al. |
| 2008/0114357 A1 | 5/2008 | Allard et al. |
| 2008/0125780 A1 | 5/2008 | Ferree |
| 2008/0177264 A1 | 7/2008 | Alamin et al. |
| 2008/0177298 A1 | 7/2008 | Zucherman et al. |
| 2008/0183209 A1 | 7/2008 | Robinson et al. |
| 2008/0262549 A1 | 10/2008 | Bennett et al. |
| 2008/0281423 A1 | 11/2008 | Sheffer et al. |
| 2008/0312693 A1 | 12/2008 | Trautwein et al. |

| | | | |
|---|---|---|---|
| 2008/0319487 | A1 | 12/2008 | Fielding et al. |
| 2009/0030457 | A1 | 1/2009 | Janowski et al. |
| 2009/0082820 | A1 | 3/2009 | Fielding et al. |
| 2009/0118766 | A1 | 5/2009 | Park et al. |
| 2009/0198282 | A1 | 8/2009 | Fielding et al. |
| 2009/0264932 | A1 | 10/2009 | Alamin et al. |
| 2009/0270918 | A1 | 10/2009 | Attia et al. |
| 2010/0004701 | A1 | 1/2010 | Malandain et al. |
| 2010/0023060 | A1 | 1/2010 | Bennett et al. |
| 2010/0036424 | A1 | 2/2010 | Fielding et al. |
| 2010/0234890 | A1 | 9/2010 | Alamin et al. |
| 2010/0234894 | A1 | 9/2010 | Alamin et al. |
| 2010/0249839 | A1 | 9/2010 | Alamin et al. |

FOREIGN PATENT DOCUMENTS

| | | |
|---|---|---|
| EP | 0 743 045 A2 | 11/1996 |
| EP | 0743045 A3 | 12/1996 |
| EP | 1 994 901 A1 | 11/2008 |
| FR | 2 681 525 A1 | 3/1993 |
| FR | 2693364 A1 | 1/1994 |
| FR | 2 714 591 | 7/1995 |
| FR | 2 717 675 A1 | 9/1995 |
| FR | 2722980 A1 | 2/1996 |
| FR | 2 828 398 A1 | 2/2003 |
| FR | 2 851 154 | 8/2004 |
| FR | 2 874 167 A1 | 2/2006 |
| FR | 2 884 136 A1 | 10/2006 |
| WO | WO 01/28442 | 4/2001 |
| WO | WO 02/03882 A2 | 1/2002 |
| WO | WO 02/03882 A3 | 5/2002 |
| WO | WO 02/051326 | 7/2002 |
| WO | WO 02/071960 | 9/2002 |
| WO | WO 03/045262 | 6/2003 |
| WO | WO 03/045262 A3 | 1/2004 |
| WO | WO 2004/052246 | 6/2004 |
| WO | WO 2004/073532 | 9/2004 |
| WO | WO 2004/073533 | 9/2004 |
| WO | WO 2005/037150 A1 | 4/2005 |
| WO | WO 2005/110258 A1 | 11/2005 |
| WO | WO 2008/051423 | 5/2008 |
| WO | WO 2008/051801 | 5/2008 |
| WO | WO 2008/051802 | 5/2008 |
| WO | WO 2008/051806 | 5/2008 |
| WO | WO 2008/051802 A3 | 7/2008 |
| WO | WO 2008/051806 A3 | 7/2008 |
| WO | WO 2008/051801 A3 | 8/2008 |
| WO | WO 2009/149407 | 12/2009 |
| WO | WO 2010/028165 | 3/2010 |
| WO | WO 2010/028165 A8 | 10/2010 |
| WO | WO 2009/149407 A9 | 2/2011 |

OTHER PUBLICATIONS

European Search Report and Search Opinion of EP Patent Application No. 07863431.8, mailed Oct. 13, 2009, 5 pages total.
Al Baz et al., "Modified Technique of Tension Band Wiring in Flexion Injuries of the Middle and Lower Cervical Spine," Spine, vol. 20, No. 11, 1995, p. 1241-1244.
Dickman et al., "Comparative Mechanical Properties of Spinal Cable and Wire Fixation Systems," Spine, vol. 22, No. 6, Mar. 15, 1997, pp. 596-604.
Garner et al., "Development and Preclinical Testing of a New Tension-Band Device for the Spine: the Loop system," European Spine Journal, vol. 11 (Suppl 2), 2002 , pp. S186-S191.
Heller, "Stability of Different Wiring Techniques in Segmental Spinal Instrumentation. An Experimental Study," Archives of Orthopedic and Trauma Surgery, vol. 117, No. 1-2, Nov. 1997, pp. 96-99.
Leahy et al., "Design of Spinous Process Hooks for Flexible Fixation of the Lumbar Spine," Proceedings of the Institution of Mechanical Engineers, Part H, Journal of Engineering in Medicine, vol. 214, No. 5, Sep. 27, 2000 , pp. 479-487.
Leahy et al., "Mechanical Testing of a Flexible Fixation Device for the Lumbar Spine," Proceedings of the Institution of Mechanical Engineers, Part H: Journal of Engineering in Medicine, vol. 214, No. 5, Sep. 27, 2000 , pp. 489-495.
Minns et al., "Preliminary Design and Experimental Studies of a Novel Soft Implant for Correcting Sagittal Plane Instability in the Lumbar Spine," Spine, vol. 22, No. 16, Aug. 15, 1997, pp. 1819-1825.
Miyasaka et al., "Radiographic Analysis of Lumbar Motion in Relation to Lumbosacral Stability: Investigation of Moderate and Maximum Motion," Spine, vol. 25, No. 6, Mar. 15, 2000, pp. 732-737.
Papp et al., "An In Vitro Study of the Biomechanical Effects of Flexible Stabilization on the Lumbar Spine," Spine, vol. 22, No. 2, Jan. 15, 1997, pp. 151-155.
Shepherd et al., "Spinous Process Strength," Spine, vol. 25, No. 3, Feb. 1, 2000, pp. 319-323.
Shepherd, "Slippage of a Spinous Process Hook During Flexion in a Flexible Fixation System for the Lumbar Spine," Medical Engineering and Physics, vol. 23, No. 2, Mar. 2001, pp. 135-141.
Voydeville et al., "Ligamentoplastie Intervertebrale Avec Cale Souple dans Les Instabilites Lombaries" <<Intervertebral Ligamentoplasty with Flexible Wedge in Lumbar Instability,>>, Orthop Traumatol, vol. 2, 1992, pp. 259-264.
International Search Report and Written Opinion of PCT Application No. PCT/US2007/081815, dated Jun. 23, 2008, 10 pages.
International Search Report and Written Opinion of PCT Application No. PCT/US2010/031471, mailed Jul. 8, 2010, 13 pages total.
European Search Opinion of EP Patent Application No. 07863431.8, mailed Jun. 4, 2010, 5 pages total.
International Search Report and Written Opinion of PCT Application No. PCT/US2010/031615, mailed Jun. 18, 2010, 9 pages total.
Frymoyer et al., "An Overview of the Incidence and Costs of Low Back Pain" Orthrop. Clin. North Am., 1991;22: 263-271.
Abbott Spine, Wallis Surgical Technique [Product Brochure], 2006; 24 pages total.
Medtronic Sofamor Danek USA, Inc., DIAM™ System Implant; 2006 [Product Brochure]; downloaded from the Internet: <http://spineinfo.ru/~files/DIAMST.pdf>, 20 pages total.
European office action dated Feb. 4, 2011 for EP Application No. 07863431.8.
European office action dated Jun. 4, 2010 for EP Application No. 07852824.7.
European office action dated Oct. 5, 2009 for EP Application No. 07852824.7.
International search report and written opinion dated Mar. 14, 2008 for PCT/US2007/022191.
International search report and written opinion dated Mar. 24, 2008 for PCT/US2007/081835.
International search report and written opinion dated May 8, 2008 for PCT/US2007/081822.

* cited by examiner

STRUCTURES AND METHODS FOR CONSTRAINING SPINAL PROCESSES WITH SINGLE CONNECTOR

CROSS REFERENCE TO RELATED APPLICATIONS

This application is a continuation-in-part of PCT Application US2007/081815, filed on Oct. 18, 2007, which claimed the benefit of Provisional Application No. 60/862,085, filed on Oct. 19, 2006, the full disclosures of which are incorporated herein by reference.

BACKGROUND OF THE INVENTION

1. Field of the Invention

The present invention relates generally to medical methods and apparatus. More particularly, the present invention relates to methods and devices for restricting spinal flexion in patients having back pain or other spinal conditions.

Figure 1:
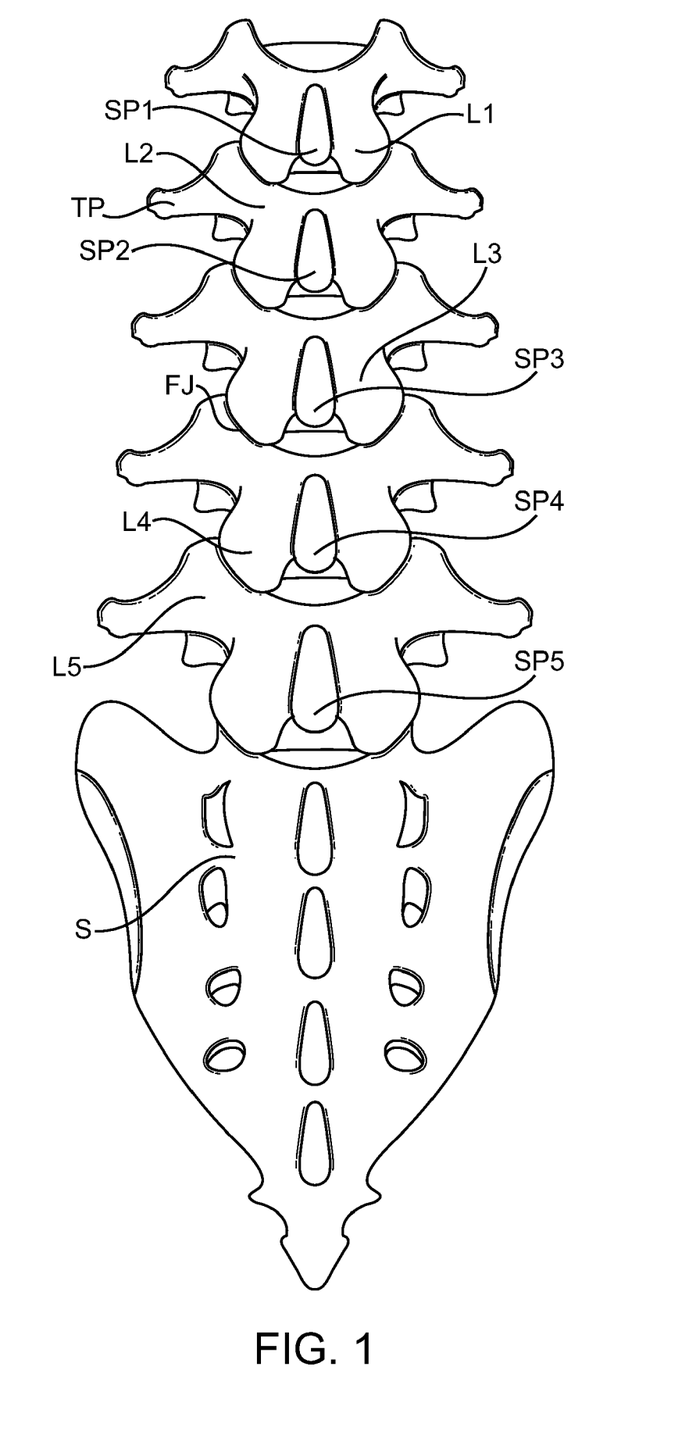
FIG. 1 is a schematic diagram illustrating the lumbar region of the spine including the spinous processes (SP), facet joints (FJ), lamina (L), transverse processes (TP), and sacrum (S).

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine (FIG. 1). Pain tends to be exacerbated when patients put their lumbar spines into flexion (i.e. by sitting or bending forward) and relieved when they put their lumbar spines into extension (i.e. arching backwards). Discogenic pain can be quite disabling, and for some patients, can dramatically affect their ability to work and otherwise enjoy their lives.

This pain experienced by patients with discogenic low back pain can be thought of as flexion instability, and is related to flexion instability that is manifested in other conditions. The most prevalent of these is spondylolisthesis, a spinal condition in which abnormal segmental translation is exacerbated by segmental flexion. The device described here should as such also be useful for these other spinal disorders associated with segmental flexion, for which the prevention or control of spinal segmental flexion is desired.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebra. Fusion is not usually recommended for discogenic pain because it is irreversible, costly, associated with high morbidity, and of questionable effectiveness. Despite its drawbacks, however, spinal fusion for discogenic pain remains common due to the lack of viable alternatives.

Recently, a less invasive and potentially more effective treatment for discogenic pain has been proposed. A spinal implant has been designed which inhibits spinal flexion while allowing substantially unrestricted spinal extension. The implant is placed over one or more adjacent pairs of spinal processes and provides an elastic restraint to the spreading apart of the spinal processes which occurs during flexion. Such devices and methods for their use are described in U.S. Patent Application 2005/02161017A1, published on Sep. 29, 2005, and having common inventors with the present application.

Figure 2:
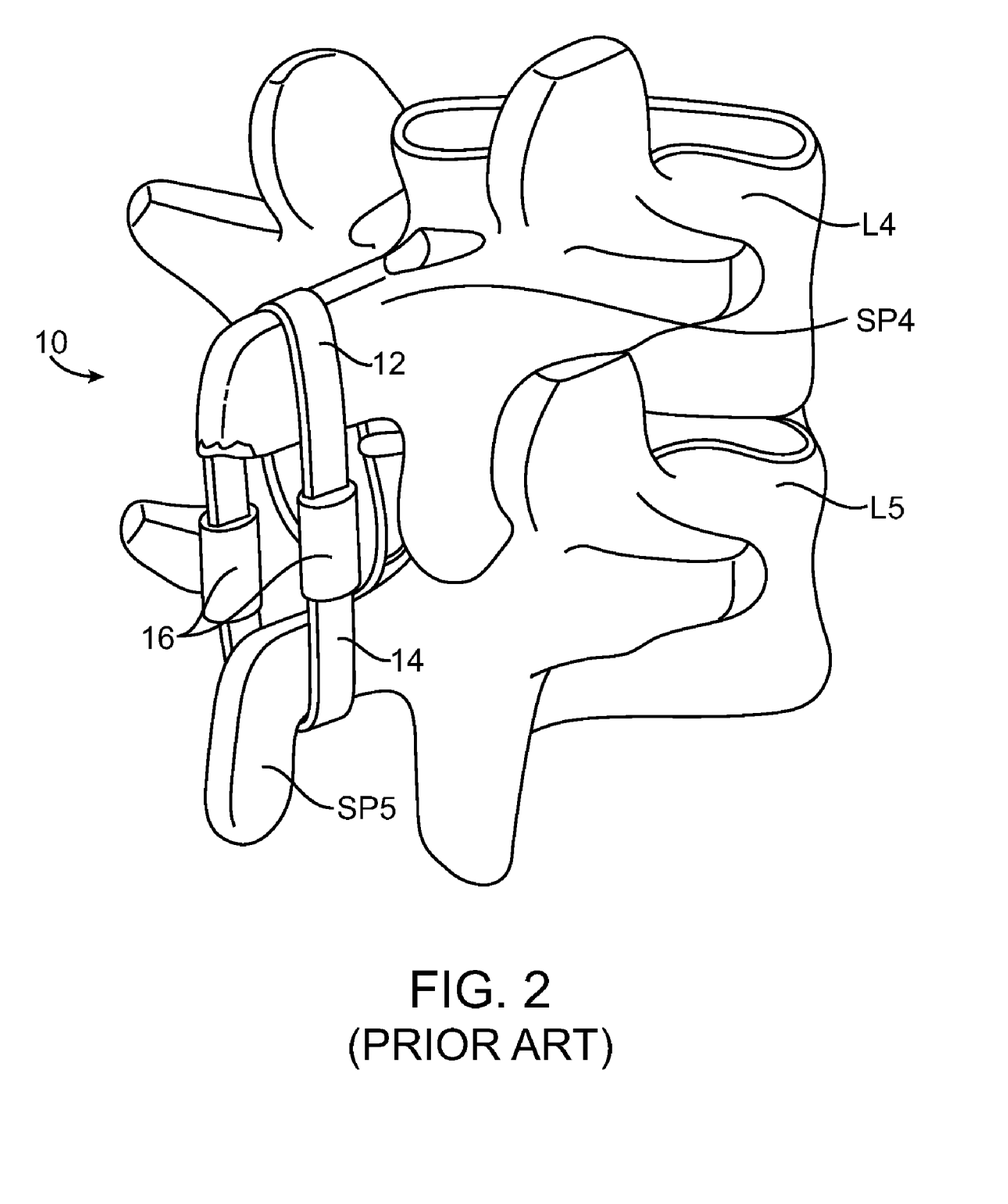
FIG. 2 illustrates a spinal implant of the type described in US 2005/0216017A1.

As illustrated in FIG. 2, an implant 10 as described in the '017 application, typically comprises an upper strap component 12 and a lower strap component 14 joined by a pair of compliant members 16. The upper strap 12 is shown disposed over the top of the spinous process SP4 of L4 while the lower strap 14 is shown extending over the bottom of the spinous process SP5 of L5. The compliant member 16 will typically include an internal element, such as a spring of rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinal processes which provides a force that resists flexion. The force increases as the processes move further apart. Usually, the straps themselves will be essentially non-compliant so that the degree of elasticity or compliance may be controlled and provided solely by the compliance members 16.

Ideally, the compliance members 16 will remain horizontally aligned and spaced generally between the spinous processes SP4 and SP5. In some instances, however, the desired symmetry may be lost if the implant structure 10 becomes circumferentially displaced about the spinous processes SP4 and SP5. Such displacement can affect the ability of the implant to provide a uniform, symmetric elastic force to inhibit flexion of the spinous processes of a spinal segment in accordance with the desired treatment. Also, the symmetric designs illustrated in FIG. 2 can be difficult to deliver from the side which would be a preferred approach in percutaneous delivery techniques.

For these reasons, it would be desirable to provide improved spinal implants and methods for their use in inhibiting flexion in patients suffering from discogenic pain. It would be particularly desirable if the improved devices would provide the desired elastic forces to the spinous processes with minimal risk of displacement or loss of symmetry of the device over time. It would be further desirable if the designs facilitated percutaneous delivery from the side and other approaches. Additionally, it would be advantageous if the implants and implantation methods could be performed with minimum tissue disruption via percutaneous and open surgical procedures. At least some of these objectives will be met by the invention as described hereinbelow.

2. Description of the Background Art

US 2005/0216017A1 has been described above. US 2006/0271055 describes a spacer having superior and inferior anchors and a spacer element therebetween. Other patents and published applications of interest include: U.S. Pat. Nos. 4,966,600; 5,011,494; 5,092,866; 5,116,340; 5,282,863; 5,395,374; 5,415,658; 5,415,661; 5,449,361; 5,456,722; 5,462,542; 5,496,318; 5,540,698; 5,609,634; 5,645,599; 5,725,582; 5,902,305; Re. 36,221; U.S. Pat. Nos. 5,928,232; 5,935,133; 5,964,769; 5,989,256; 6,053,921; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; Published U.S. Patent Application Nos. US 2002/0151978; US 2004/0024458; US 2004/0106995; US 2004/0116927; US 2004/0117017; US 2004/0127989; US 2004/0172132; US 2005/0033435; US 2005/0049708; US 2006/0069447; Published PCT Application Nos. WO 01/28442 A1; WO 02/03882 A2; WO 02/051326 A1; WO 02/071960 A1; WO 03/045262 A1; WO 2004/052246 A1; WO 2004/073532 A1; and Published Foreign Application Nos. EP 0322334 A1; and FR 2 681 525 A1.

BRIEF SUMMARY OF THE INVENTION

The present invention provides spinal implants and methods for restricting flexion of spinal segments for the treatment of discogenic pain and other spinal conditions, such as spondylolisthesis, where a physician may desire to control segmental flexion. Systems according to the present invention include spinous process constraint structures comprising a first attachment element adapted to be placed over a first spinous process, a second attachment element adapted to be placed over a second spinous process, and a single connector joining the first attachment element and the second attachment element. By "single connector," it is meant that the connector joins a single point or location on the first attachment element to a single point or location on the second attachment element. In contrast, the prior connectors shown in FIG. 2, for example, provide a pair of connection points and two connectors for joining the upper component 12 to the lower strap component 14. Use of the single connector for joining the first and second attachment elements reduces the likelihood that the attachment members will become displaced such that the desired symmetric attachment geometry becomes asymmetric. A single connector also reduces the need to balance the elastic forces being applied to the opposite sides of the spinous processes. The single connector will also simplify alignment of the implant during implantation, thus simplifying percutaneous implantation and potentially minimizing tissue disruption in both percutaneous and other implantation protocols.

The single connector may comprise a single elastic member, where the single elastic member may itself comprise a continuous length of elastic material having uniform or non-uniform elastic properties along said length. Alternatively, the connector may comprise an elastic member including two or more separate components, for example inelastic or non-compliant straps, cables, or other flexible members attached to a compliance member which provides the desired elasticity. Different embodiments for the compliance members are described in co-pending, commonly owned application No. 12/106,103, filed on Apr. 18, 2008, the full disclosure of which is incorporated herein by reference. Regardless of the particular structure, the single connector and/or elastic member will provide an elastic stiffness in tension between the attachment members in the range from 7.5 N/mm to 50 N/mm, preferably from 10 N/mm to 25 N/mm, and usually in the range from 10 N/mm to 15 N/mm. In addition to providing such elastic stiffness in tension, the single connector and/or elastic member will be constructed to provide little or no elastic stiffness in compression. Usually, the elastic stiffness in compression will be below 3 N/mm, preferably below 0.5 N/mm. The ability of the constraint structures of the present invention to provide a targeted elastic stiffness in tension while providing little or no elastic stiffness in compression allows for treatment of patient's having spinal segments where the kinematics are improved by application of the elastic force to the spine in flexion while providing little or no elastic resistance to extension.

The first and second attachment elements may have similar or different geometries. Exemplary geometries include open hook structures which may be placed about the spinous processes and which have a single attachment point for connection to the single connector. The attachment elements may also be loop structures which fully circumscribe the spinous process, where the loop is provided with a single connection point for connection to the single connector. Often, the attachment elements will be placed over the spinous process without further attachment. In other instances, however, it may be desirable to provide a secondary attachment to the spinous process, such as staples, pins, screws, sutures, adhesives, energy-mediated attachments (such as laser welding), or the like. In some instances, one of the two attachment elements may be adhered to the adjacent spinous process while the other of the attachment elements may be simply placed over the adjacent spinous process without adherence.

The constraint structures of the present invention may comprise separate components which are joined or connectable together. For example, each of the first attachment element, the second attachment element, and the single connector may be formed separately and interconnected by conventional techniques, such as screwing, welding, linking with male and female attachment members, strapping, soldering, or any other such fastening technique. In other instances, any two or more of the components of the constraints of the present invention may be integrally or monolithically formed from a common structural member. For example, a pair of hook-like elements may be integrally formed with an intermediate connector by forming the components from a single rod, wire, cable, polymer substrate, or the like.

The constraint structures of the present invention may be symmetric or asymmetric. For example, when loops or other attachment elements circumscribe the spinous processes the connector may comprise a single axial member lying on the midline or mid-plane which bisects the spinous processes. Such a symmetric structure is advantageous since it applies an axial force generally free from lateral components to the loops which constrain the spinous processes.

In other instances, however, it will be desirable to position the single connector on a side of the spinous processes so that the connector does not need to pass through the region between the spinous processes. Such asymmetric constraint structures thus reduce or eliminate the need to penetrate the interspinous/supraspinous ligaments lessening patient trauma and facilitating placement protocols. For such asymmetric designs, the attachment member may be a simple pin, screw, or other fastener which penetrates the body of the spinous process, but will more usually be a hook, loop, or other member which can attach to the spinous process without necessarily penetrating therethrough. For example, when using hooks, the upper attachment member can be placed over a superior surface of the superior spinous process while a lower hook member may be placed around the inferior surface of the inferior spinous process.

When a single connector lies asymmetrically relative to the plane of the spinous processes, the connector will place the attachment members under a rotational load, often causing the single connector to bow inward toward the spinous process plane. Such deformation of the single connector will also tend to rotate and displace the attachment members, particularly those which are not fixedly attached to the spinous processes. In order to reduce such deformation and improve the stability of the spinous process constraints, a reinforcement member may be placed on or over the single connector, particularly within the region between the spinous processes. For example, a reinforcement sleeve may be placed coaxially over at least a portion of the single connector. Alternatively, and particularly when a compliance member is included in the single connector (as described in more detail below) the reinforcement member may be a slide assembly which is attached to the connector at a superior location and an inferior location and which can extend and contract together with elongation and contraction of the single connector while still maintaining alignment between the superior and inferior segments thereof.

In another aspect of the present invention, the attachment members may be hinged or pivotally connected to the single connector to facilitate introduction and implantation of the constraint structure in a patient. For example, superior and inferior hooks may be pivotally attached at the upper and lower ends of a single connector so that the hooks may be folded to reduce the profile of the constraint as it is being introduced into position adjacent to the spinous processes. Once in position, the hooks or other attachment members may then be pivoted or otherwise moved into place around the spinous processes to provide the desired constraint.

In yet another specific aspect of the present invention, the attachment members may comprise clamps or similar structures which may be placed over posterior surfaces of the spinous processes to hold a single connector therebetween. Such posterior access is advantageous since it reduces the need to disrupt the/supraspinous ligament. Thus the use of clamps or attachment members which are placed over the posterior surface of the spinous processes is particularly advantageous when used in connection with an asymmetric single connector so that the penetration of the supraspinous/ ligaments is minimized.

The spinous process constraints of the present invention may further comprise a compliance member disposed within or as part of the single connector. The compliance member may have any structure which provides for the desired elasticity in the connector to permit the first and second attachment elements to spread apart as the spinal segment undergoes flexion. Suitable compliance members are described in published U.S. Application No. 2005/0216017 A1, which has been previously incorporated herein by reference.

In other embodiments, the single connector may comprise an elastomeric body which is disposed between the first and second attachment elements. In some instances, the elastomeric body may be positionable over the supraspinous ligament, and in certain of those cases such elastomeric bodies may be adapted to be sutured or otherwise attached to the supraspinous ligament.

In a further aspect of the present invention, methods for restricting flexion of a spinal segment comprise positioning a first attachment element on a first spinous process and positioning a second attachment element on a second spinous process, wherein the attachment members are joined by a single connector. The attachment members may be positioned in an open surgical procedure through the supraspinous ligament or may be percutaneously implanted, optionally from a single sided posterior approach avoiding the need to penetrate the supraspinous ligament. In a specific embodiment, the elements are joined with an elastic member, where the elastic member is preferably positioned over the supraspinous ligament. In particular embodiments, the methods further comprise attaching the elastic member to the supraspinous ligament, for example by suturing. Usually, the methods further comprise penetrating the supraspinous ligament to permit passage of the attachment element(s) and/or the elastic member therethrough. Still further optionally, the attachment members may be attached to the spinous processes, typically by stapling or any of the other attachment modalities described above.

BRIEF DESCRIPTION OF THE DRAWINGS

FIGS. 8A and 8B illustrate use of a reinforcement member on a single connector which does not include a compliance member, while

FIGS. 16A and 16B illustrate a connector similar to that shown in FIGS. 15A and 15B which further includes a compliance member. In FIG. 16B, placement of the constraint adjacent to the supraspinous/interspinous ligaments is illustrated.

DETAILED DESCRIPTION OF THE INVENTION

Figure 3:
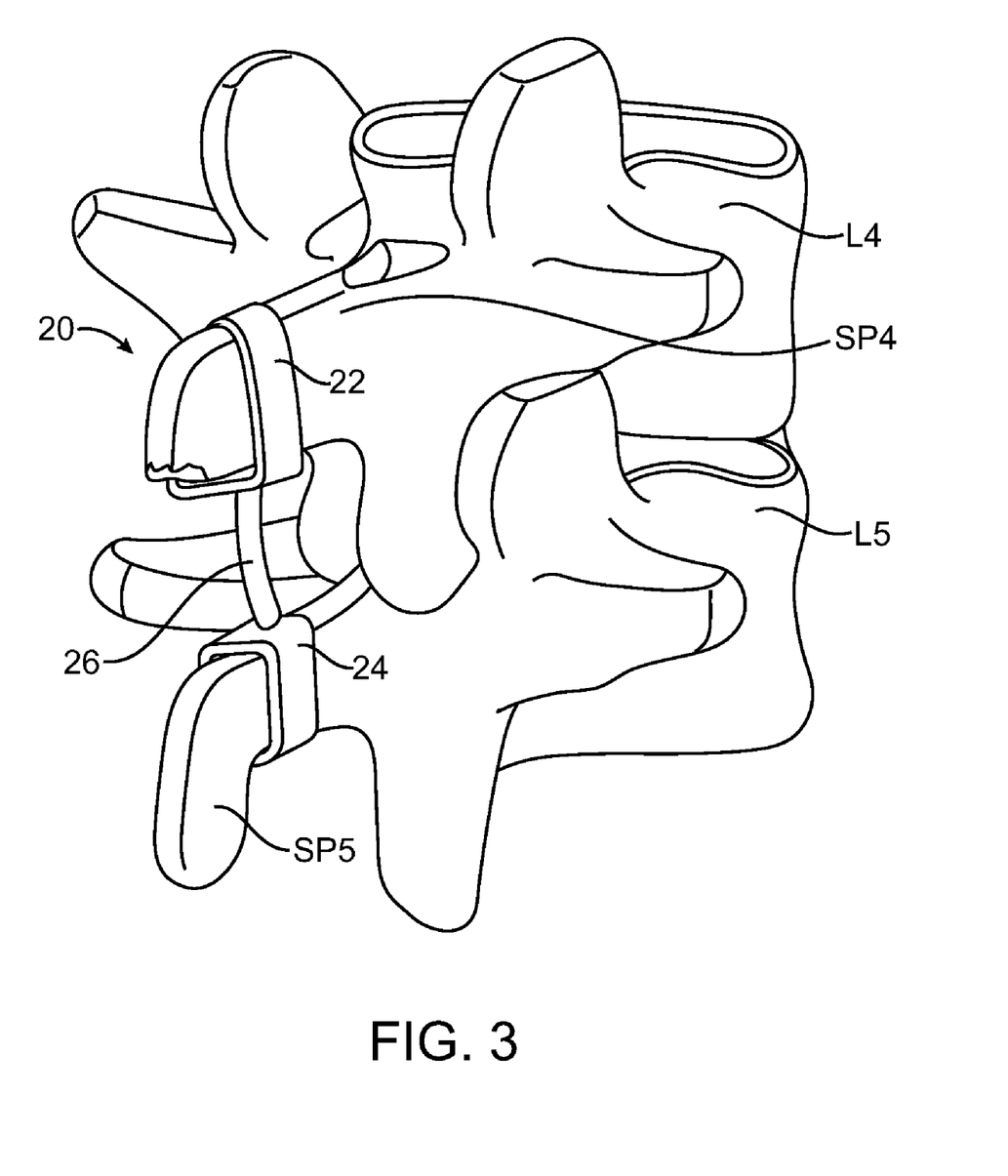
FIG. 3 illustrates an exemplary embodiment of a spinous process constraint structure constructed in accordance with the principles of the present invention.

Referring now to FIG. 3, a spinous process constraint structure 20 constructed in accordance with the principles of the present invention comprises a first or upper attachment member 22 and a second or lower attachment member 24. The first and second attachment members are connected by a single connector 26, shown in the form of an elastic rod or cable. Usually, the attachment members 22 and 24 will be non-distensible, and will be firmly placed over the spinous processes, shown as the spinous process SP4 of L4 and the spinous process SP5 of L5. The connector 26 will be elastically distensible so that it will comprise an elastic constraining force as a spinal segment undergoes flexion which causes the spinous processes SP4 and SP5 to spread vertically apart. While being elastic in tension, the single connector 26 will have a very low column strength so that it exerts very little force on the spinous processes SP4 and SP5 when the spinal segment is in extension and the processes move vertically toward one another. As used herein, the phrase "spinal segment" is synonymous with the phrase "functional spinal unit (FSU)" and intended to mean the smallest physiological motion unit of the spine that exhibits biomechanical characteristics similar to those of the entire spine. A spinal segment or FSU consists of two adjacent vertebrae, the intervertebral disc and all adjoining ligaments between them and excludes other connecting tissues such as muscles. The three-joint complex that results is sometimes referred to as the "articular triad." Another term for the FSU is spinal motion segment. These definitions are taken from White A A, Panjabi M M. (1990), *Clinical Biomechanics of the Spine*, Philadelphia, JB Lippincott.

Figure 4:
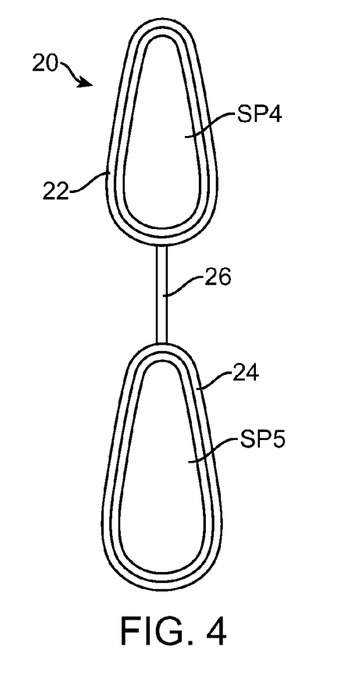
FIGS. 4-11 are schematic illustrations of additional exemplary embodiments of the spinous process constraint structures of the present invention, where the adjacent spinous processes are shown in section.

The first and second attachment members 22 and 24 may be wrapped around the associated spinous process SP4 and SP5 without further adherence or fastening. In some cases, however, it may be desirable to staple, suture, glue, or otherwise attach the attachment members to the underlying spinous process. It will also be appreciated that in many instances the attachment members may have a seam or closure which allows them to be wrapped around the spinous process and closed in situ thereover during an implantation procedure. It will be further appreciated that the single connector 26 may be preattached to either or both of the attachment members 22 and 24. In other instances, however, it may be desirable to attach the connector 26 to either or both of the attachment members 22 and 24 during the implantation procedure in order to permit the length of the connector to be adjusted. In particular, it will be desirable that the length of the connector 26 be selected so that the connector is generally fully extended but not under significant tension when the spinal segment is in its neutral (non-flexion and non-extension) condition. In such cases, the connector 26 will begin to apply tension on the spinous processes 22 and 24 as soon as they begin to undergo flexion while collapsing and applying no force on the spinous processes as they undergo extension. FIG. 4 is a schematic cross-sectional view of the spinous process constraint structure 20 of FIG. 3.

Figure 5:
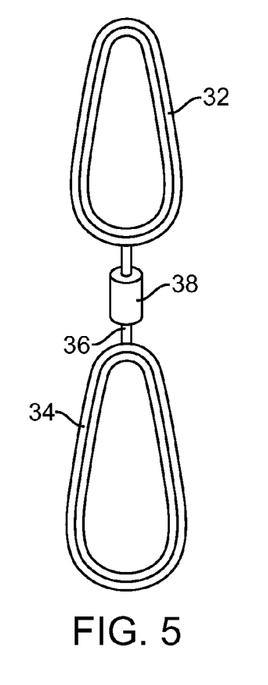

FIG. 5 illustrates an alternative spinous process constraint structure 30 having first and second attachment members 32 and 34, similar to those described in connection with FIGS. 3 and 4, and joined by a single connector 36 having a compliance member 38. In this embodiment, the single connector 36 may be formed from a non-distensible material where the desired elasticity is provided by the compliance member 38.

Figure 6:
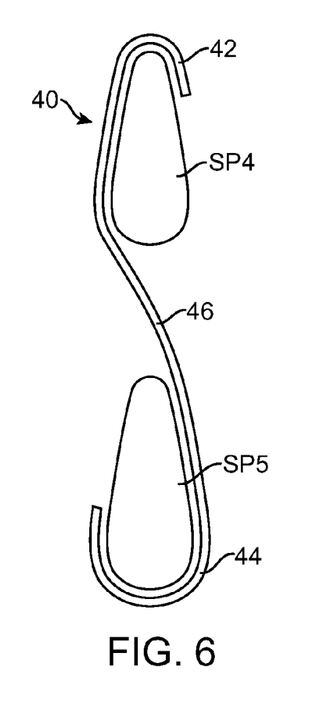

Referring now to FIG. 6, a spinous process constraint structure 40 having a first or upper hook-like attachment member 42 and a second or lower hook-like attachment member 44 is illustrated. The first and second attachment members 42 and 44 are connected by a single contiguous or integral connector 46, which is transversely oriented in the space between the upper spinous process SP4 and the lower spinous process SP5. The constraint structure 40 may be formed from a spring-like metal, such as spring steel or nickel-titanium alloy, or alternatively may be formed from an elastomeric polymer. In some instances, the hook-like attachment members could be reinforced or otherwise modified to be substantially non-compliant, while the connector 46 could be modified to enhance its elasticity, for example having a serpentine or coil spring structure.

Figure 7:
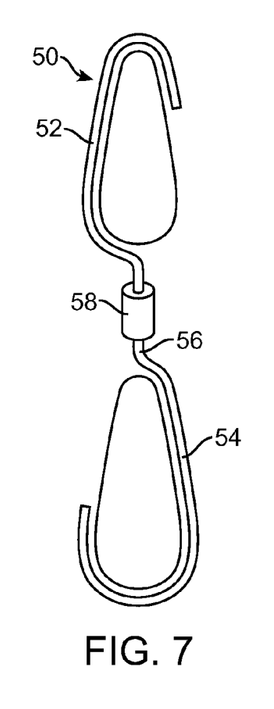

Referring now to FIG. 7, a further spinous process constraint system 50 comprises upper and lower hook-like attachment members 52 and 54 joined by a single connector 56. The upper and lower attachment members 52 and 54 as well as the connector section 56 may be formed from metal or polymer and will typically be non-distensible. The desired elasticity between the attachment members is provided by a compliance member 58.

Figure 8:
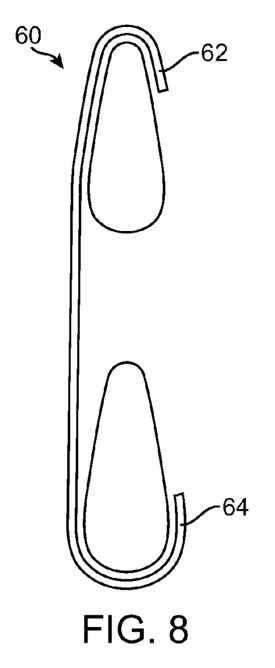
Figure 8A:
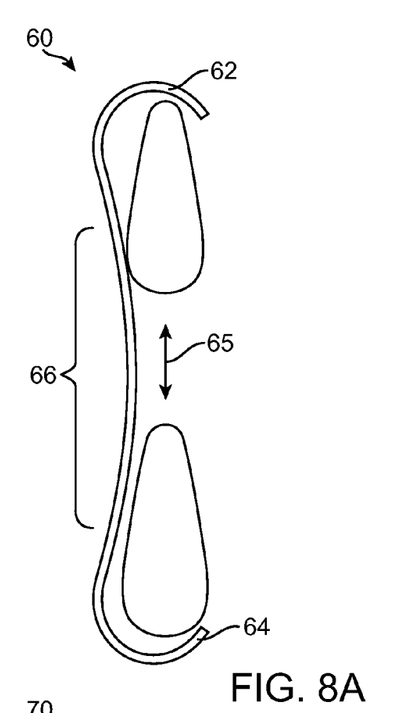

Referring now to FIG. 8, yet another spinous process constraint system 60 comprises first and second hook-like attachment members 62 and 64. Instead of being connected in an S-shaped pattern, as shown in FIG. 6, the hook members 62 and 64 are connected in a C-shaped pattern, as shown in FIG. 8. Other aspects of the constraint system 60 may be similar to those described with respect to constraint 40 of FIG. 6.

Figure 8B:
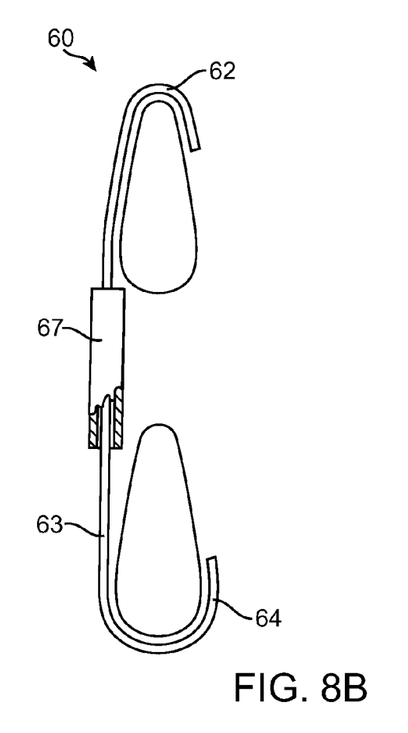

The spinous process constraint 60 of FIG. 8 will have a tendency to deform when placed under an axial load as the spinous processes undergo a flexion causing movement in the direction of arrow 65. Typically, a region 66 of the constraint will tend to bow inwardly which causes the superior and inferior hook members 62 and 64 to displace laterally, increasing the risk that they will shift from their intended positions on the spinous processes. In order to alleviate this condition, a reinforcement member 67 can be placed over a portion of the single connector 63 between the hooks 62 and 64. The reinforcement member may be a simple sleeve constructed from a relatively rigid material, such as a metal or rigid polymer, having a central passage which is placed over the single connector. Other reinforcement structures would also be possible. Additionally, the sleeve embodiment shown in FIG. 8B could be modified to be used with constraint embodiments including compliance members as described elsewhere in this application.

Figure 9:
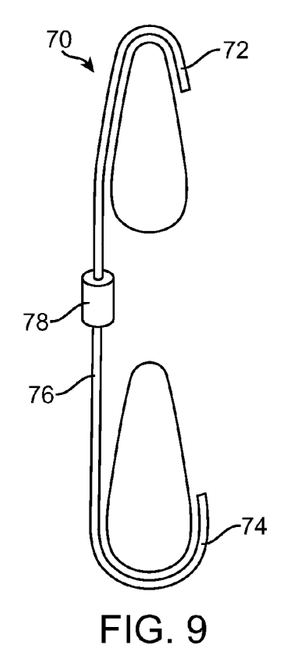

Similarly, as shown in FIG. 9, a spinous process constraint system 70 comprises first and second hook-like attachment members 72 and 74 arranged in C-shaped pattern, generally as shown in FIG. 8, further comprises compliance member 78 attached to superior and inferior segments of the single connector 76 (which is preferably non-compliant). Other aspects of the system may be generally as described in connection with the constraint structure 50 of FIG. 7.

Figure 9A:
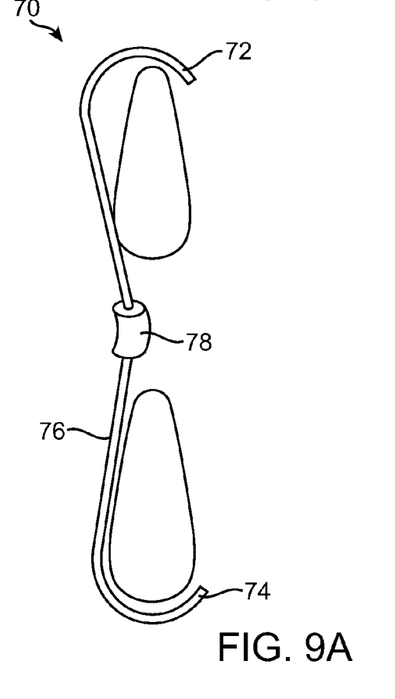
FIGS. 9A and 9B illustrate use of a reinforcement member on a single connector which includes a compliance member.
Figure 9B:
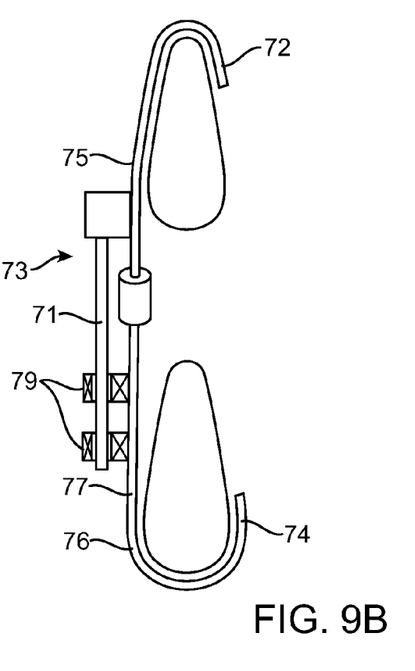

The spinous process constraint 70 of FIG. 9 can also undergo deformation when subjected to an axial load, as shown in FIG. 9A. A reinforcement assembly 73 specifically adapted for constraints having compliance members 78 is illustrated in FIG. 9B. The reinforcement assembly 73 connects to a superior segment 75 of the single connector 76 and includes a slide rod 71 extending toward an inferior segment 77 of the single connector 76. The slide rod 71 is received in a bearing structure 79 attached to the interior segment 77 which allows the rod to translate as the segments 73 and 77 move toward and away from each other as the spine undergoes extension and flexion. The reinforcement assembly 71 helps maintain the proper alignment between the superior and inferior segments 75 and 77 to prevent the bowing and deformation illustrated in FIG. 9A.

Figure 10:
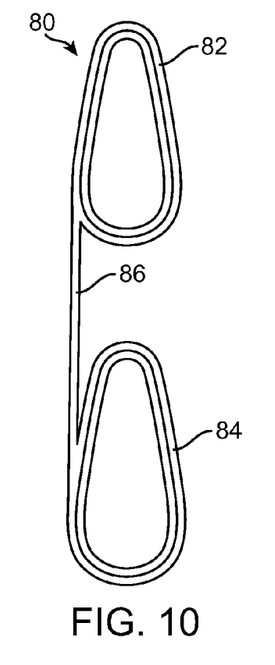

In still another embodiment, a spinous process constraint system 80, as shown in FIG. 10, comprises a loop or encircling first attachment member 82 and a loop or encircling second attachment member 84. The attachment members 82 and 84 are joined by a connector 86 which, instead of being attached at the center of the attachment members, is attached laterally to one side. It will be appreciated that the connector 86 could just as well have been attached laterally on the opposite side.

Figure 11:
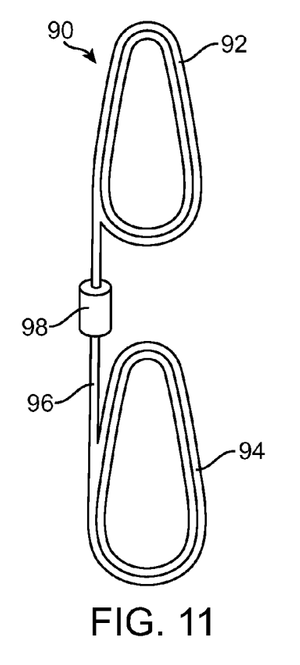

Referring now to FIG. 11, spinous process constraint system 90 comprises upper and lower attachment members 92 and 94 which are similar to those described with respect to constraint structure 80 of FIG. 10. A single connector 96 is typically formed from a non-distensible material, and the desired elasticity is provided by a compliance member 98 provided along the length of the single connector 96.

Figure 12:
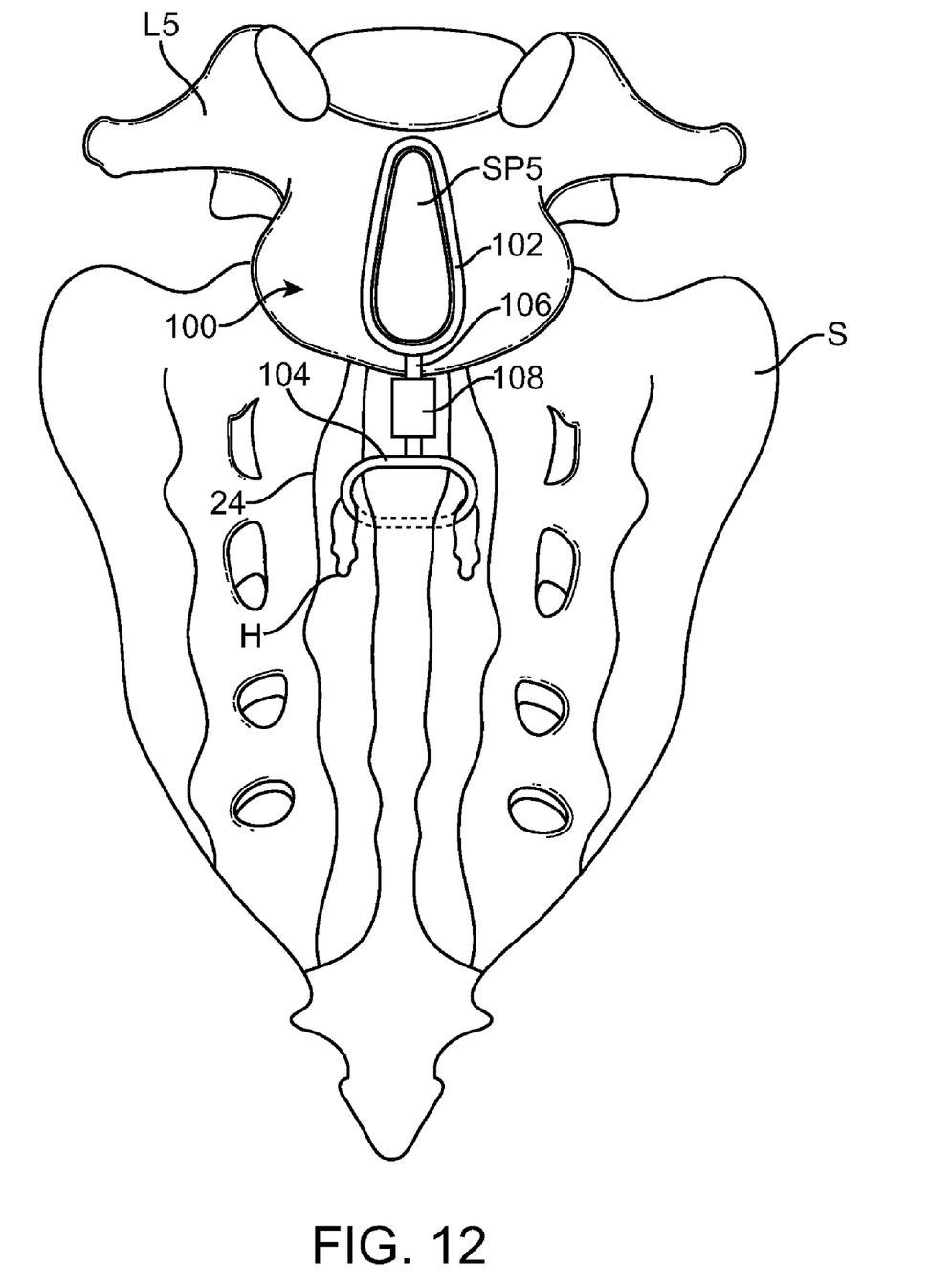
FIG. 12 illustrates a further alternative embodiment of a spinal constraint structure of the present invention shown with a first attachment member placed over the spinous process of L5 and a lower attachment member attached to the sacrum.

As described thus far, spinous process constraint systems have been intended to be placed on adjacent spinous processes. It will be appreciated that the constraint systems could be placed on spinous processes which are non-adjacent; e.g., separated by one or more additional spinous processes. It will be further appreciated that the spinous process constraint systems could be attached at a first or upper end to the spinous process SP5 of L5 and at a second or lower end to the sacrum S, as shown in FIG. 12. As the sacrum will often not include a process or other structure sufficient for attachment, when attachment member as described previously, spinous process constraint system 100 may include a first or upper attachment member 102 similar to any of those described previously, and a second or lower attachment member 104 which is modified to attach to the sacrum, e.g., by looping through a hole H formed in the structure of the sacrum. Other attachment members suitable for attaching to the sacrum are described in copending application No. 11/827,980, filed on Jul. 13, 2007, the full disclosure of which is incorporated herein by reference. A single connector 106 is provided between the upper and lower attachment members 102 and 104, optionally including a compliance member 108 to provide the desired elasticity.

Figure 13:
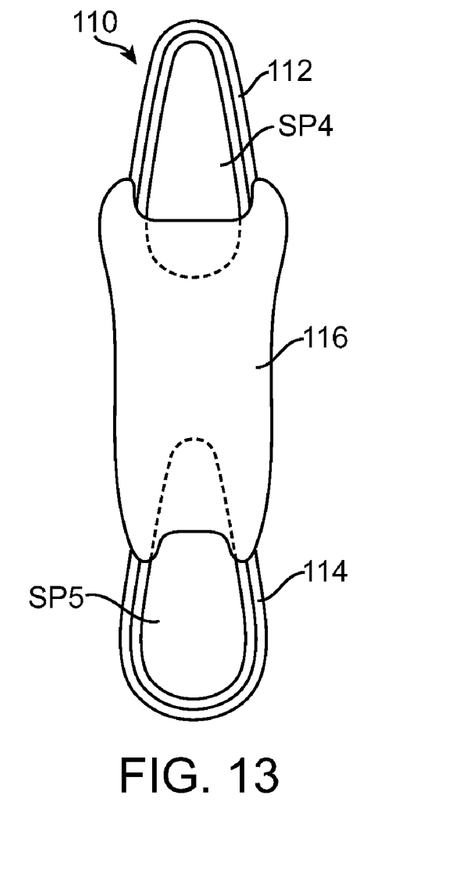
FIGS. 13 and 14 illustrate yet another embodiment of a spinous process constraint structure of the present invention where the attachment members are placed over adjacent spinous processes with the single connector passing through and over the supraspinous ligament.
Figure 14:
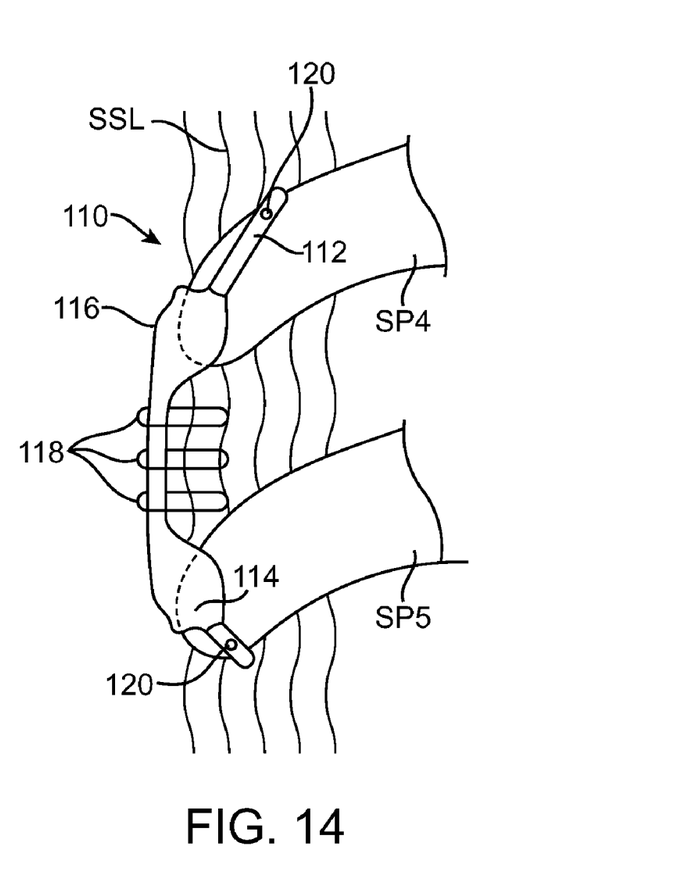

Referring now to FIGS. 13 and 14, yet another alternative spinous process constraint system and method for its implementation are described. The spinous processes constraint system 110 includes a first or upper attachment member 112 and a second or lower attachment member 114. The upper and lower attachment members are joined by an elastic component, typically an elastomeric body 116 which is configured to be placed over the surface of the supraspinous ligament SSL, as shown in FIG. 14. The advantage of the constraint structure 110 is that it will minimally disrupt the structure of the supraspinous ligament, typically requiring only minor penetrations to allow the placement of the attachment members 112 and 114. Optionally, the elastomeric body 116 may be attached to the supraspinous ligament SSL, for example by sutures 118, or adhesives, staples, or by other conventional attachment means. Similarly, because the elastomeric body 116 will be exerting a rearward force on the attachment members 112 and 114, it will typically be desirable to staple, pin, suture, glue, or otherwise attach the attachment members to the spinous processes SP4 and SP5. While pins 120 are shown, it will be appreciated that any of the other attachment means could also be used.

Figure 15A:
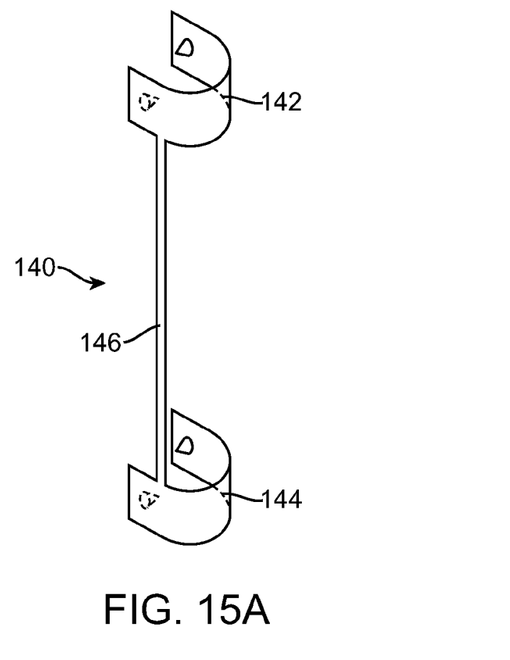
FIGS. 15A and 15B illustrate a spinous process constraint having a pair of clamps suitable for engaging posterior surfaces of a pair of adjacent spinous processes.
Figure 15B:
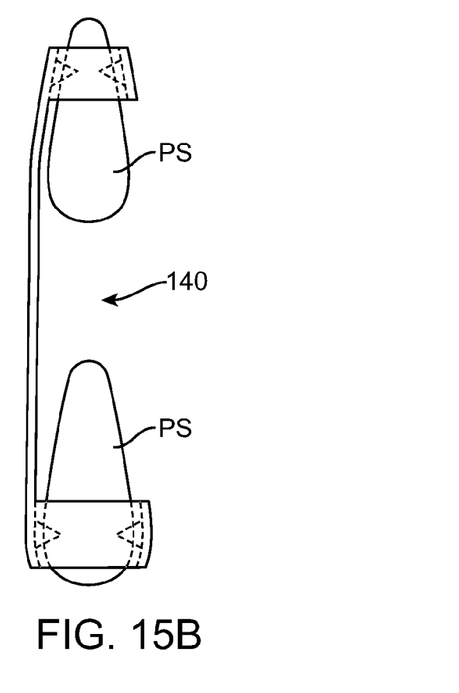

Referring to FIGS. 15A and 15B, a spinous process constraint structure 140 comprises a superior clamp 142, an inferior clamp 144, and a single connector comprising an axial member 146 therebetween. The axial member 146 may have any of the structures described previously to provide the desired elasticity and modulation of flexion. The clamps 142 and 144 are formed so that they may be placed over the posterior surfaces PS of the spinous processes to be constrained, as shown in FIG. 15B. By employing clamps which are located over the posterior surfaces and further employing a laterally displaced axial member 146 which is on the side of the spinous processes, the need to penetrate or otherwise disturb the supraspinous and interspinous ligaments is minimized.

Figure 16A:
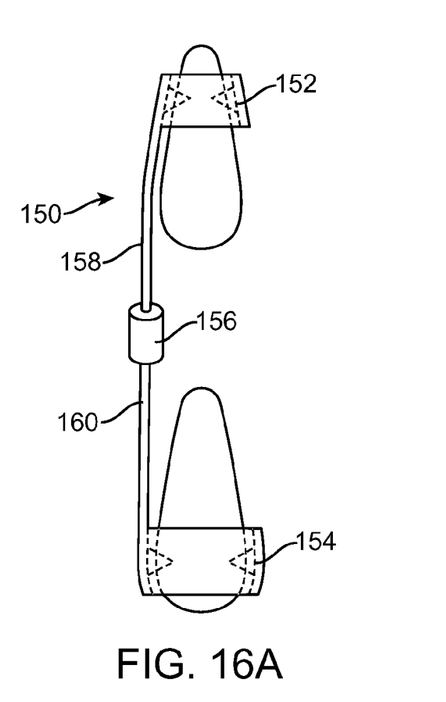
Figure 16B:
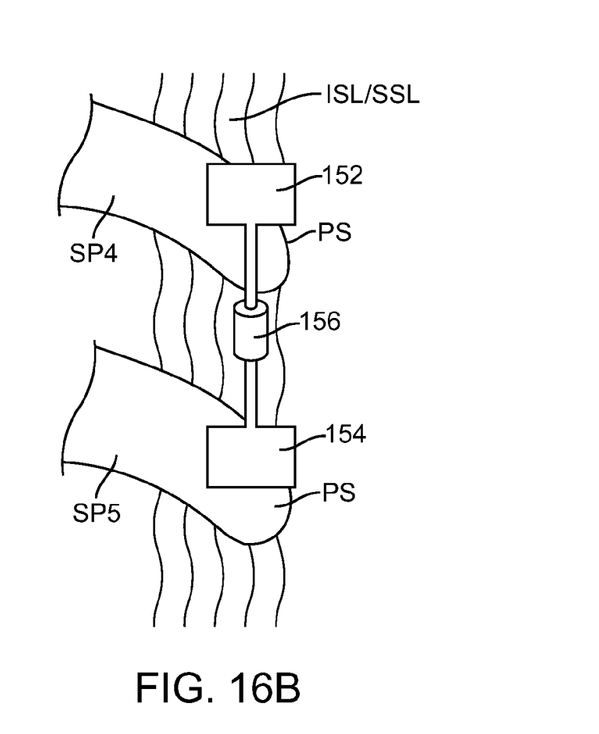

Referring to FIGS. 16A and 16B, a spinous process constraint 150 having a superior clamp structure 152 and an inferior clamp structure 154 is illustrated. The constraint 150 is similar to that illustrated in FIGS. 15A and 15B, but further includes a compliance member 156 which joins a superior segment 158 and inferior segment 160 of a single connector between the clamps 152 and 154. Placement of the spinous process constraint 150 on spinous processes SP4 and SP5 is illustrated in FIG. 16B. The clamps 152 and 154 placed over the posterior surfaces PS of the spinous processes so that minimum intrusion is made into the interspinous and supraspinous ligaments ISL/SSL. Similarly, as the single connector and compliance member 156 are on one side of the spinous processes, intrusion into the interspinous and supraspinous ligaments is further reduced.

Figure 17:
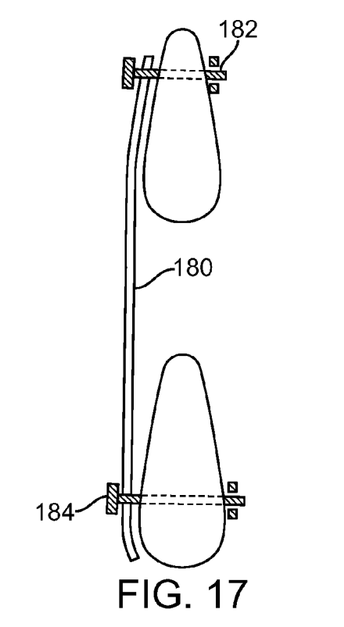
FIG. 17 illustrates a further exemplary embodiment of a spinous process constraint according to the present invention, shown with an asymmetric axial member connected using pins to the spinous processes.
Figure 18:
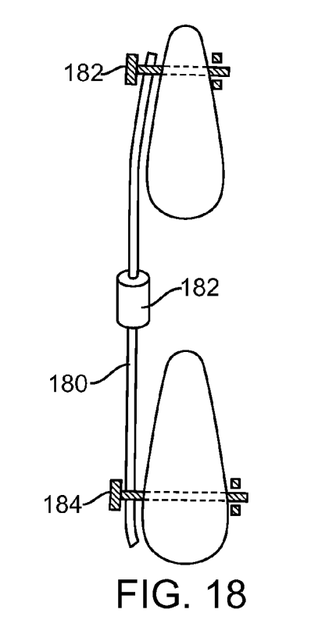
FIG. 18 illustrates a spinous process constraint similar to that shown in FIG. 17, further including a compliance member.

Other asymmetric spinous process constraint structures may be constructed in accordance with the principles of the present invention. As shown in FIG. 17, for example, a single connector 180 may be connected between pins 182 and 184 which are penetrated through the bodies of superior and inferior spinous processes. The single connector 180 may also include a compliance member 182, as shown in FIG. 18.

Figure 19:
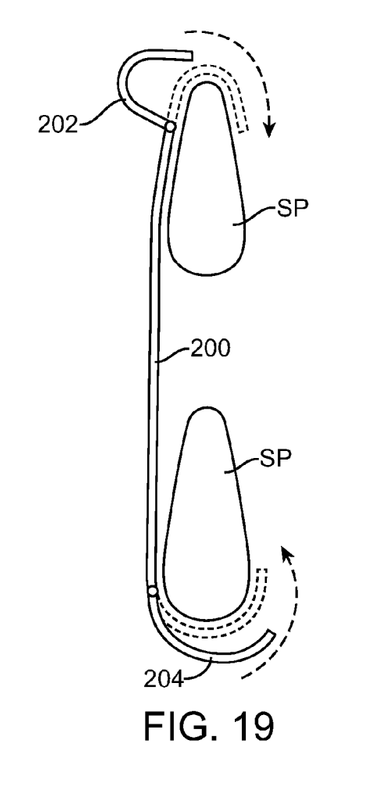
FIG. 19 illustrates a spinous process constraint according to the present invention having pivoted hooks for attachment of adjacent spinous processes.
Figure 20:
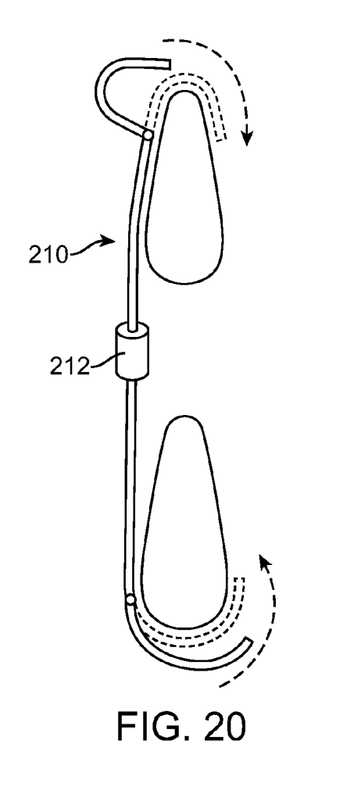
FIG. 20 illustrates a spinous process constraint similar to that shown in FIG. 19, but further including a compliance member.

As shown in FIGS. 19 and 20, a spinous process constraint may comprise a single, continuous structure 200 having a superior hook 202 and an inferior hook 204. The superior and inferior hooks 202 and 204 are pivotally attached to an axial portion of the constraint therebetween. The constraint 200 may be introduced to a position laterally adjacent to the spinous processes SP with the hooks 202 and 204 in retracted configuration. Once the constraint is in place on one side of the spinous processes, hooks 202 and 204 may be pivoted back over the superior and inferior surfaces of the spinous processes, as illustrated. A similar spinous process constraint structure 210 having a compliance member 212 is illustrated in FIG. 20. Introduction of the constraint structure 210 may be performed in the same manner as constraint structure 200.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for restricting flexion of a spinal segment, said method comprising:
   positioning a first attachment element on a first spinous process;
   positioning a second attachment element on a second spinous process or a sacrum;
   wherein the attachment elements are joined only with a single elastic member which is positioned over or adjacent to the supraspinous and interspinous ligaments, and
   wherein only the single elastic member extends between the first spinous process and the second spinous process or the sacrum;
   providing an elastic stiffness in tension that resists flexion of the spinal segment without resisting extension thereof; and
   attaching the elastic member to the supraspinous ligament.

2. A method as in claim 1, wherein the elastic member provides an elastic stiffness in tension between said attachment elements in the range from 7.5 N/mm to 50 N/mm.

3. A method as in claim 2, wherein the elastic stiffness is in the range from 10 N/mm to 25 N/mm.

4. A method as in claim 3, wherein the elastic stiffness is in the range from 10 N/mm to 15 N/mm.

5. A method as in claim 2, wherein the elastic member provides an elastic stiffness in compression between said elements below 3 N/mm.

6. A method as in claim 5, wherein said elastic stiffness in compression is below 0.5 N/mm.

7. A method as in claim 1, wherein the elastic member is an elastomeric body which is sutured to the supraspinous ligament.

8. A method as in claim 1, further comprising penetrating the supraspinous ligament to permit passage of the attachment element(s) and/or elastic member therethrough.

9. A method as in claim 1, further comprising attaching the attachment members to the spinous process and/or the sacrum.

10. A method as in claim 1, wherein the attachment elements and elastic member are introduced percutaneously.

11. A method as in claim 10, wherein the attachment elements and elastic member are introduced laterally from one side of the midline.

12. A method as in claim 11, wherein the elements and member are introduced from a posterior approach from one side of the midline.

13. A method as in claim 1, wherein the attachment members are clamped over posterior surfaces of the spinous processes.

14. A method as in claim 13, wherein the elastic member is positioned along one side of each spinous process.

15. A method as in claim 1, further comprising reinforcing the single connector to limit deformation under axial load.

16. A method as in claim 15, wherein reinforcing comprises placing a reinforcement sleeve over the single connector.

17. A method for restricting flexion of a spinal segment with a constraint structure, said method comprising:
providing the constraint structure, the constraint structure comprising a first attachment element and a second attachment element;
positioning the first attachment element on a first spinous process; and
positioning the second attachment element on a second spinous process or a sacrum;
wherein the attachment elements are joined only with a single connector extending therebetween, and
wherein only the single connector extends between the first spinous process and the second spinous process or the sacrum, and
wherein the constraint structure provides an elastic stiffness in tension that resists flexion of the spinal segment while still permitting extension thereof, and
wherein the attachment elements comprise hooks and positioning comprises introducing the hooks in a retracted configuration and pivoting the hooks relative to the single connector to capture the spinous processes after the connector is positioned adjacent the spinous processes.

18. A method as in claim 17, wherein the single connector provides an elastic stiffness in tension between said attachment elements in the range from 7.5 N/mm to 50 N/mm.

19. A method as in claim 18, wherein the elastic stiffness is in the range from 10 N/mm to 25 N/mm.

20. A method as in claim 19, wherein the elastic stiffness is in the range from 10 N/mm to 15 N/mm.

21. A method as in claim 18, wherein the single connector provides an elastic stiffness in compression between said elements below 3 N/mm.

22. A method as in claim 21, wherein said elastic stiffness in compression is below 0.5 N/mm.

23. A method as in claim 17, further comprising attaching the attachment members to the spinous process and/or the sacrum.

24. A method as in claim 17, wherein the attachment elements and elastic member are introduced percutaneously.

25. A method as in claim 24, wherein the attachment elements and elastic member are introduced laterally from one side of the midline.

26. A method as in claim 24, wherein the elements and member are introduced from a posterior approach from one side of the midline.

27. A method as in claim 17, wherein a superior hook is pivoted over a superior surface of a superior spinous process and an inferior hook is pivoted over an inferior surface of an inferior spinous process.

28. A method as in claim 17, further comprising reinforcing the single connector to limit deformation under axial load.

29. A method as in claim 28, wherein reinforcing comprises placing a reinforcement sleeve over the single connector.

30. A method as in claim 28, wherein the single connector includes a compliance member and reinforcing comprises placing a slide assembly adjacent to the compliance member, said slide assembly aligning superior and inferior segments of the single connector.

31. A method for restricting flexion of a spinal segment, said method comprising:
positioning a first attachment element on a first spinous process;
positioning a second attachment element on a second spinous process or a sacrum;
wherein the attachment elements are joined only with a single elastic member which is positioned over or adjacent to the supraspinous and interspinous ligaments, and
wherein only the single elastic member extends between the first spinous process and the second spinous process or the sacrum;
providing an elastic stiffness in tension that resists flexion of the spinal segment without resisting extension thereof; and
penetrating the supraspinous ligament to permit passage of the attachment element(s) and/or elastic member therethrough.

32. A method as in claim 31, wherein the elastic member provides an elastic stiffness in tension between said attachment elements in the range from 7.5 N/mm to 50 N/mm.

33. A method as in claim 32, wherein the elastic stiffness is in the range from 10 N/mm to 25 N/mm.

34. A method as in claim 33, wherein the elastic stiffness is in the range from 10 N/mm to 15 N/mm.

35. A method as in claim 32, wherein the elastic member provides an elastic stiffness in compression between said elements below 3 N/mm.

36. A method as in claim 35, wherein said elastic stiffness in compression is below 0.5 N/mm.

37. A method as in claim 31, further comprising attaching the elastic member to the supraspinous ligament.

38. A method as in claim 37, wherein the elastic member is an elastomeric body which is sutured to the supraspinous ligament.

39. A method as in claim 31, further comprising attaching the attachment members to the spinous process and/or the sacrum.

40. A method as in claim 31, wherein the attachment elements and elastic member are introduced percutaneously.

41. A method as in claim 40, wherein the attachment elements and elastic member are introduced laterally from one side of the midline.

42. A method as in claim 41, wherein the elements and member are introduced from a posterior approach from one side of the midline.

43. A method as in claim 31, wherein the attachment members are clamped over posterior surfaces of the spinous processes.

44. A method as in claim 43, wherein the elastic member is positioned along one side of each spinous process.

45. A method as in claim 31, further comprising reinforcing the single connector to limit deformation under axial load.

46. A method as in claim 45, wherein reinforcing comprises placing a reinforcement sleeve over the single connector.

47. A method for restricting flexion of a spinal segment with a constraint structure, said method comprising:
- providing the constraint structure, the constraint structure comprising a first attachment element and a second attachment element;
- positioning the first attachment element on a first spinous process; and
- positioning the second attachment element on a second spinous process or a sacrum;
- wherein the attachment elements are joined only with a single connector extending therebetween, and
- wherein only the single connector extends between the first spinous process and the second spinous process or the sacrum, and
- wherein the constraint structure provides an elastic stiffness in tension that resists flexion of the spinal segment while still permitting extension thereof; and
- further comprising penetrating the supraspinous ligament to permit passage of the attachment element(s) and/or elastic member therethrough.

48. A method as in claim 47, wherein the single connector provides an elastic stiffness in tension between said attachment elements in the range from 7.5 N/mm to 50 N/mm.

49. A method as in claim 48, wherein the elastic stiffness is in the range from 10 N/mm to 25 N/mm.

50. A method as in claim 49, wherein the elastic stiffness is in the range from 10 N/mm to 15 N/mm.

51. A method as in claim 48, wherein the single connector provides an elastic stiffness in compression between said elements below 3 N/mm.

52. A method as in claim 51, wherein said elastic stiffness in compression is below 0.5 N/mm.

53. A method as in claim 47, further comprising attaching the attachment members to the spinous process and/or the sacrum.

54. A method as in claim 47, wherein the attachment elements and elastic member are introduced percutaneously.

55. A method as in claim 54, wherein the attachment elements and elastic member are introduced laterally from one side of the midline.

56. A method as in claim 54, wherein the elements and member are introduced from a posterior approach from one side of the midline.

57. A method as in claim 47, wherein the attachment elements comprise hooks and positioning comprises introducing the hooks in a retracted configuration and pivoting the hooks relative to the single connector to capture the spinous processes after the connector is positioned adjacent the spinous processes.

58. A method as in claim 47, wherein a superior hook is pivoted over a superior surface of a superior spinous process and an inferior hook is pivoted over an inferior surface of an inferior spinous process.

59. A method as in claim 47, further comprising reinforcing the single connector to limit deformation under axial load.

60. A method as in claim 59, wherein reinforcing comprises placing a reinforcement sleeve over the single connector.

61. A method as in claim 59, wherein the single connector includes a compliance member and reinforcing comprises placing a slide assembly adjacent to the compliance member, said slide assembly aligning superior and inferior segments of the single connector.

\* \* \* \* \*